United States Patent [19]
Kaplan et al.

[11] B 3,985,747
[45] Oct. 12, 1976

[54] CRYSTALLINE SESQUIHYDRATE OF 7-[D-α-AMINO-α-)p-HYDROXYPHENYL)ACETAMIDO]-3-(1,2,3-TRIAZOL-5-YLTHIOMETHYL)-3-CEPHEM-4-CARBOXYLIC ACID

[75] Inventors: Murray Arthur Kaplan, Syracuse; Alphonse Peter Granatek, Baldwinsville, both of N.Y.

[73] Assignee: Bristol-Myers Company, New York, N.Y.

[22] Filed: May 24, 1974

[21] Appl. No.: 473,039

[44] Published under the second Trial Voluntary Protest Program on February 10, 1976 as document No. B 473,039.

[52] U.S. Cl. .............................. 260/243 C; 424/246
[51] Int. Cl.² ....................................... C07D 501/20
[58] Field of Search ................................. 260/243 C

[56] References Cited
UNITED STATES PATENTS

| | | | |
|---|---|---|---|
| 3,641,021 | 2/1972 | Ryan .............................. | 260/243 C |
| 3,674,776 | 7/1972 | Long et al. ..................... | 260/243 C |
| 3,759,904 | 9/1973 | Crast .............................. | 260/243 C |
| 3,855,213 | 12/1974 | Dunn et al. .................... | 260/243 C |

*Primary Examiner*—Nicholas S. Rizzo
*Attorney, Agent, or Firm*—David M. Morse

[57] ABSTRACT

The crystalline sesquihydrate of 7-[D-α-amino-α-(p-hydroxyphenyl)acetamido]-3-(1,2,3-triazol-5-ylthiomethyl)-3-cephem-4-carboxylic acid is prepared and found to be a stable useful form of the cephalosporin antibiotic particularly advantageous for pharmaceutical formulations.

1 Claim, No Drawings

CRYSTALLINE SESQUIHYDRATE OF 7-[D-α-AMINO-α-(P-HYDROXYPHENYL)-)ACETAMIDO]-3-(1,2,3-TRIAZOL-5-YLTHIOMETHYL)-3-CEPHEM-4-CARBOXYLIC ACID

BACKGROUND OF THE INVENTION

1. Field of the Invention.

The crystalline cephalosporin hydrate of the present invention possesses in general the usual attributes of that family of antibacterial agents and is particularly useful in the treatment of bacterial infections by both oral and parenteral administration.

2. Description of the Prior Art.

The literature concerning this class of antibacterial agents has been reviewed frequently; two recent reviews are The Cephalosporins Microbiological, Chemical and Pharmacological Properties and Use in Chemotherapy of Infection, L. Weinstein and K. Kaplan, Annals of Internal Medicine, 72, 729–739 (1970) and Structure Activity Relationships Among Semisynthetic Cephalosporins, M. L. Sassiver and A. Lewis, Advances in Applied Microbiology, edited by D. Perlman, 13, 163–236 (1970), Academic Press, New York. Additional reviews which pay particular attention to the patent literature are found in U.S. Pat. Nos. 3,776,907, 3,776,175 and 3,759,904. Solvates, and hydrates in particular, are often encountered in the cephalosporin field, e.g. U.S. Pat. Nos. 3,280,118, 3,502,663, 3,655,656, 3,692,781, 3,708,478 and 3,714,157.

7-[D-α-Amino-α-(p-hydroxyphenyl)acetamido]-3-(1,2,3-triazol-5-ylthiomethyl)-3-cephem-4-carboxylic acid is a new cephalosporin, also called BL-S640, which is described and claimed by my colleagues David Willner and Leonard B. Crast, Jr. in U.S. application Ser. No. 318,340 filed Dec. 26, 1972; the entire disclosure of that application is incorporated herein by reference.

In the preparation of 7-[D-α-amino-α-(p-hydroxyphenyl)acetamido]-3-(1,2,3-triazol-5-ylthiomethyl)-3-cephem-4-carboxylic acid by the procedures disclosed in the above-mentioned U.S. applicatian Ser. No. 318,340, the crude amorphous product obtained in chemical production is rather heavily contaminated with residues of the reagents and with various decomposition products from which it can not be separated in reasonable yield by recrystallization or the other usual techniques such as washing with solvents. All efforts to purify the amorphous crude product by forming a crystalline zwitterion or a hydrate thereof by conventional methods, e.g. crystallization from an aqueous reaction mixture by adjustment of the pH to the isoelectric point, have failed. The problem of purifying this particular cephalosporin is further complicated by the fact that at alkaline pH, i.e. pH 7.0 or higher, the compound degrades very rapidly by loss of the thiol moiety.

In an attempt to isolate and purify the amorphous 7-[D-α-amino-α-(p-hydroxyphenyl)acetamido]-3-(1,2,3-triazol-5-ylthiomethyl)-3-cephem-4-carboxylic acid, the amorphous crude product has been successfully converted into a crystalline methanol solvate. This methanolate, however, is undesirable for human pharmaceutical use because of the toxicity of methanol. In addition the methanol solvate provides little purification of the crude product as measured by any increase in biopotency, decrease in color or reduction in impurity content. An ethanol solvate has also been prepared and, while crystalline, its formation was not accompanied by any significant purification. When suspended in water, moreover, the ethanolate gradually lost its ethanol to change into a solid tacky form which lost crystallinity, did not suspend evenly and gummed. No way was found to remove the solvents from the solvates in order to obtain essentially anhydrous pure compound and the products so obtained became tacky and were not useful for pharmaceutical formulations. Lyophilization of water solutions of the methanol or ethanol solvates (5 – 10 mg./ml.) gave an amorphous monohydrate product which was biologically unstable (lost 37% of its potency when stored at 56° C. for 1 month) and unacceptable for pharmaceutical use.

It was an objective of the present invention to provide a stable, nontoxic, non-solvated crystalline hydrate of 7-[D-α-amino-α-(p-hydroxyphenyl)acetamido]-3-(1,2,3-triazol-5-ylthiomethyl)-3-cephem-4-carboxylic acid which would be substantially free of impurities and useful in preparing pharmaceutical dosage forms of the cephalosporin antibiotic for both oral and parenteral administration.

The present invention provides a novel crystalline sesquihydrate of 7-[D-α-amino-α-(p-hydroxyphenyl)acetamido]-3-(1,2,3-triazol-5-ylthiomethyl)-3-cephem-4-carboxylic acid and processes for its preparation. The hydrate of the present invention is a particularly useful form of the above-mentioned cephalosporin in that it is produced substantially free of the impurities found in samples of the cephalosporin made by practical commercial processes. In addition, it possesses good biological stability (as a solid it loses less than 6% of its bioactivity when stored for 1 month at 56°C.) and the desirable physical properties needed for formulation into both oral and parenteral dosage forms. When suspended in water the crystalline sesquihydrate does not lose biological activity and does not undergo deleterious changes on standing such as loss of crystallinity, uneven suspension, oiling, clumping, settling or tackiness. The crystalline sesquihydrate is a useful broad-spectrum antibacterial agent and is found to provide effective blood levels on both oral and parenteral administration.

The novel crystalline form of 7-[D-α-amino-α-(p-hydroxyphenyl)acetamido]-3-(1,2,3-triazol-5-ylthiomethyl)-3-cephem-4-carboxylic acid sesquihydrate described and claimed herein exhibits essentially the following X-ray powder diffraction properties:

| Line | Spacing d(A) | Relative Intensity |
| --- | --- | --- |
| 1 | 9.31 | 45 |
| 2 | 6.77 | 93 |
| 3 | 6.17 | 32 |
| 4 | 5.56 | 14 |
| 5 | 4.42 | 100 |
| 6 | 3.97 | 76 |
| 7 | 3.78 | 95 |
| 8 | 3.55 | 55 |
| 9 | 3.41 | 53 |
| 10 | 3.10 | 26 |
| 11 | 3.01 | 19 |
| 12 | 2.94 | 9 |
| 13 | 2.83 | 17 |
| 14 | 2.77 | 23 |
| 15 | 2.55 | 19 |
| 16 | 2.32 | 10 |
| 17 | 2.23 | 12 |
| 18 | 2.05 | 10 |
| 19 | 1.97 | 6 |
| 20 | 1.88 | 7 |

The details for this determination of X-ray diffraction properties are as follows:

A small amount of sample was sealed in a 0.2 mm. diameter low scattering glass capillary tube which was mounted for exposure in a 114.6 mm. diameter Debye-Scherrer powder diffraction camera. The exposure time was 8 hours on a Norelco X-ray Generator operated at 35 KV-20 mA using a standard focus copper target X-ray tube (weighted CuK wavelength $\lambda=1.5418$ A). Kodak No-Screen X-Ray Film was used and developed for 3 minutes at 20° C. in Kodak Liquid X-ray Developer.

A very small amount of crystalline sodium fluoride was mixed in with some samples to provide internal calibration. In addition, a sample of pure NaF was run through the complete procedure for the same purpose.

The films were read on a Norelco Debye-Scherrer film reader, recording the positions of the diffraction rings to the nearest 0.05 mm. The data were corrected for film shrinkage and the interplanar spacings ($d$-spacings) were calculated from the corrected data. A computer program (XRAY, by P. Zugenmaier) was used for all calculations. The accuracy in the resulting $d$-spacing data was ~1%.

An intensity record of all films was obtained using a Joyce-Loeble Mark IIIC Recording Microdensitometer (scan ratio 5:1, 0.1 O.D. wedge). Relative intensities on a scale 1–100 were assigned to all recognizable diffraction rings using peak intensities corrected for the background reading.

A sample of the crystalline sesquihydrate product was subjected to IR and NMR analyses and the functional group data from the spectra are summarized below:

| IR (as KBr disc) | |
|---|---|
| 2400 – 3600 cm$^{-1}$ | (broad overlapping peaks) amide NH, NH$_3^+$, OH(H$_2$O) |
| 1780 | β-lactam C=O |
| 1707 | amide C=O |
| 1570 | COO$^-$ |
| 1520 | aromatic C=C |
| NMR (DMSO, dilute DCl) | |
| 7.96 ppm γ | singlet, 1H, H$_a$ |
| 6.7 – 7.6 | multiplet, 4H, H$_b$ |
| 5.7 | doublet, 1H, H$_c$ |
| 4.9 – 5.2 | multiplet, 2H, H$_d$, H$_e$ |
| 3.2 – 4.2 | multiplet, 4H, H$_g$, H$_f$ |
| 1.1 | doublet* |

* residual propylene glycol.

which process comprises suspending 7-[D-α-amino-α-(p-hydroxyphenyl)acetamido]-3-(1,2,3-triazol-5-ylthiomethyl)-3-cephem-4-carboxylic acid methanol solvate in water at a pH range of approximately 2.5 – 7.0 and recovering the desired crystalline sesquihydrate product from the aqueous reaction mixture.

A preferred embodiment of the present invention is a process for the preparation of crystalline 7-[D-α-amino-α-(p-hydroxyphenyl)acetamido]-3-(1,2,3-triazol-5-ylthiomethyl)-3-cephem-4-carboxylic acid sesquihydrate; which process comprises treating an aqueous suspension of 7-[D-α-amino-α-(p-hydroxyphenyl)acetamido]-3-(1,2,3-triazol-5-ylthiomethyl)-3-cephem-4-carboxylic acid methanol solvate with sufficient base to raise the pH of the aqueous suspension to between about 6 and 7 and preferably in the range of about 6.2 – 6.7 at a temperature in the range of about 5° C. to 85° C. for a period of time of from about 1 to 24 hours; recovering the crystalline hydrate from the aqueous reaction mixture and air drying at a temperature between about 37°–45°C. to produce the desired crystalline sesquihydrate product.

The methanol solvate of 7-[D-α-amino-α-(p-hydroxyphenyl)acetamido]-3-(1,2,3-triazol-5-ylthiomethyl)-3-cephem-4-carboxylic acid is slurried in water to form an aqueous suspension having a pH in the range of about 3–4. The methanol solvate starting material may be prepared directly from the crude amorphous cephalosporin zwitterion by the procedures described in U.S. application Ser. No. 318,340, e.g. crystallization from a methanol solution of the crude zwitterion, or by the improved procedures described below in the section entitled "Preparation of the Starting Materials". Most advantageously, however, the crude cephalosporin zwitterion is recovered as the methanol solvate, the methanol solvate is converted to a propylene glycol solvate and the propylene glycol solvate finally reconverted to a purer crystalline methanol solvate which is employed as starting material in the process of the present invention for preparation of the crystalline sesquihydrate. The procedures for preparing the methanol and propylene glycol solvates are described below in the "Preparation of the Starting Materials" section. The above-mentioned preferred purification procedure minimizes the impurities found in the methanolate starting material and results in production of the highest quality hydrate product. Since water does not appear to replace propylene glycol residues in the crystal-

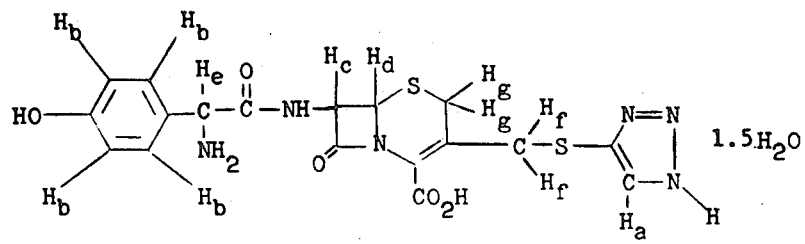

The crystalline sesquihydrate has a decomposition range of 188°–194° C. and, when observed under a polarizing microscope, appears as micro crystals. The sesquihydrate has a solubility in water of approximately 10 mg./ml. at 25° C.

The present invention further provides a process for the preparation of crystalline 7-[D-α-amino-α-(p-hydroxyphenyl)acetamido]-3-(1,2,3-triazol-5-ylthiomethyl)-3-cephem-4-carboxylic acid sesquihydrate;

line methanolate, it is also desirable to use methanol solvate which is substantially free of propylene glycol impurities. This propylene glycol-free methanol solvate may be prepared for example by recrystallizing the methanolate from methanol until substantially all of the propylene glycol impurities have been removed. The aqueous suspension of methanol solvate may be of any desired concentration, but it is preferred for highest yields to employ a concentration of about 250 mg.

methanolate per ml. water. The methanolate is preferably ground to a particle size of less than 200 mesh.

After preparing the aqueous suspension of methanol solvate and preferably stirring for a period of time of from about 1 to 24 hours, the crystalline hydrate may be recovered from the aqueous reaction mixture by conventional methods such as filtration or centrifugation. The product is washed with water and air dried at a temperature of between about 37°C. and 45°C. preferably for a period of from about 24 to 48 hours.

In the preferred method the methanol solvate is slurried in water to form a aqueous suspension and the pH of the suspension is then slowly raised to a value such that the maximum amount of crystalline hydrate crystallizes out of the reaction mixture. Best results are obtained when the pH is raised by addition of base to about 6–7 and most preferably in the range of about 6.2 – 6.7. The nature of the base used to effect the pH change is not important and any water-miscible base is acceptable. The most preferred bases because of availability and cost are the alkali metal hydroxides, e.g. sodium or potassium hydroxide. The base is added slowly with stirring for a time sufficient to cause precipitation of the desired crystalline hydrate. The formation of the crystalline hydrate is believed to occur in a short time but it is preferred to stir the reaction mixture for a period of from about 1 to 24 hours, most preferably about 2 hours, so as to permit complete reaction and formation of good quality crystals. The temperature of the reaction mixture during the pH adjustment step is not particularly critical and may advantageously be in the range of from about 5° C. to 85° C. Most conveniently, however, the entire process is carried out at room temperature.

The crystalline sesquihydrate is recovered from the reaction mixture by conventional methods such as filtration or centrifugation, washed with water and air dried at temperatures in the range of about 37° – 45° C. preferably for a period of time of from about 24–48 hours.

A slight variation of the above preferred process comprises adding the methanolate starting material directly to an aqueous solution having a pH of about 6–7 and most preferably in the range of about 6.2 – 6.7. The aqueous methanolate suspension is then slurried preferably for between about 1 to 24 hours and the crystalline hydrate recovered as described above.

Upon recovery of the crystalline hydrate from the reaction mixture and cooling to room temperature, the hydrate is ordinarily isolated in the form of the crystalline dihydrate. The dihydrate is found to lose one-half molecule of bound water under very mild conditions, however, and thus air drying of the product hydrate at a temperature in the range of about 37° – 45° C. for 24 hours will convert the dihydrate to the more stable sesquihydrate crystalline product. Air drying of the crystalline dihydrate at room temperature for a period of about 24 hours in the presence of dry laboratory air has also been found to result in conversion to the preferred crystalline sesquihydrate form. The crystalline sesquihydrate of the present invention may be subjected to more extreme drying conditions, i.e. air drying at temperatures above about 45° C. and/or vacuum drying to form other crystalline hydrates having lesser amounts of bound water. Thus, the crystalline sesquihydrate having 1.5 moles of water per mole of cephalosporin zwitterion can be converted to a crystalline monohydrate by air drying at 56° C. for 24 hours. Upon vacuum drying at 56° C. for 24 hours a crystalline hemihydrate is formed having 0.5 moles of bound water per mole of cephalosporin. All of the above-mentioned novel crystalline hydrates are included within the scope of the present invention.

When tested in vitro and in vivo, the crystalline 7-[D-$\alpha$-amino-$\alpha$-(p-hydroxyphenyl)acetamido]-3-(1,2,3-triazol-5-ylthiomethyl)-3-cephem-4-carboxylic acid sesquihydrate of this invention exhibits substantially the same potency and spectrum of activity reported in U.S. application Ser. No. 318,340.

In the treatment of bacterial infections in man, the crystalline 7-[D-$\alpha$-amino-$\alpha$-(p-hydroxyphenyl)-acetamido]-3-(1,2,3-triazol-5-ylthiomethyl)-3-cephem-4-carboxylic acid sesquihydrate is administered either orally or parenterally, as preferred by the physician, in an amount of from about 5 to 200 mg./kg./day and preferably about 5 to 20 mg./kg./day in divided dosage, e.g. three or four times a day. It is administered in dosage units containing, for example, 125, 250 or 500 mg. of active ingredient with suitable physiologically acceptable carriers or excipients. The dosage units may be in solid form such as tablets or capsules or liquid form such as aqueous solutions or suspensions.

PREPARATION OF STARTING MATERIALS

D-(-)-2-(p-hydroxphenyl)glycyl chloride hydrochloride was prepared in a high state of purity and very efficiently by the following procedure:

10.0 g. (about 0.06 moles) of D-(-)-2-(p-hydroxyphenyl)glycine (U.S. Pat. No. 3,489,752) was slurried in 100 ml. of dioxane. The slurry was stirred and $COCl_2$ (phosgene) was passed in while the slurry temperature was held at 50°–58° C. The $COCl_2$ was passed in for a total time of 3.5 hours. A yellow solution was obtained. The solution was purged with nitrogen to expel the excess $COCl_2$. HCl gas was bubbled through the solution for 2.5 hours. The solution was stirred and a small amount was diluted with some ether to obtain some crystals which were added to the batch as seed. The solution was stirred at 20°–25° C. for 16 hours. The resulting slurry of crystalline D-(-)-2-(p-hydroxyphenyl)glycyl chloride hydrochloride was filtered to collect the product. The filter-cake was washed with dioxane and methylene chloride and then dried in a vacuum desiccator over $P_2O_5$. The yield of D-(-)-2-(p-hydroxyphenyl)glycyl chloride hydrochloride was 7.3 g.

IR - excellent.

| Elemental Analysis: | | | | |
|---|---|---|---|---|
| | Cl | C | H | N |
| Theory | 31.93 | 43.14 | 4.09 | 6.37 |
| Found | 31.96 | 42.46 | 4.22 | 6.56 |
| Acid Chloride Assay: | | | | |
| Acid Chloride | — 98.6% | | | |
| Free COOH | — None | | | |
| Free HCl | — None | | | |

D-$\alpha$-t-Butoxycarbonylamino-$\alpha$-(p-hydroxyphenyl)acetic acid

In a three necked flask equipped with a reflux condenser, overhead stirrer and thermometer, there was placed a well mixed mixture of 8.36 g. (0.05 mole) of D-(-)-p-hydroxyphenylglycine and 3.02 g. (0.075 mole) of magnesium oxide in 120 ml. of 50% aqueous dioxane. The mixture was stirred for 1 hr. and then treated with 10.74 g. (0.075 mole) of t-butoxycarbonylazide. The mixture was then stirred and heated at 45°–50° for 17 hours under $N_2$. The solution was diluted with 400 ml. of $H_2O$ and extracted twice with 300 ml. of ethyl acetate. The aqueous phase was acidified with 10% citric acid solution to pH 4 and saturated with NaCl. The aqueous mixture was extracted with 3 × 400 ml. of ethyl acetate. The solution was dried over $Na_2SO_4$ and the solvent evaporated. The residue was triturated with "Skellysolve B" to yield D-α-t-butoxycarbonylamino-α-(p-hydroxyphenyl)acetic acid as a solid weighing 10.4 g. (78.5%).

7-[D-α-t-Butoxycarbonylamino-α-(p-hydroxyphenyl)acetamido]-31(1,2,3-triazol-5-ylthiomethyl)-3-cephem-4-carboxylic acid To a suspension of 7-amino-3-(1,2,3-triazol-5-ylthiomethyl)-3-cephem-4-carboxylic acid (6.0 g., 19.0 mmole) in 100 ml. dry methylene chloride there was added 8.5 ml. of 1,1,1,3,3,3-hexamethyldisilazane (40.9 mmole). The mixture was stirred and heated at reflux for 4 hours at which time a clear solution was obtained. The solvent was evaporated and the residual oil was subjected to high-vacuum overnight at room temperature. The foamy residue was dissolved in 85 ml. of dry THF and cooled to about −15° before introduction into the subsequent reaction mixture.

D-α-t-Butoxycarbonylamino-α-(4-hydroxyphenyl)acetic acid, (4.4 g., 16.5 mmole) was dissolved in 145 ml. dry THF. The solution was stirred and cooled to −20°.

N-methylmorpholine (1.6 g., 16 mmoles) and isobutylchloroformate (2.3 g., 16.8 mmole) were added in succession at such rate that the temperature of the mixture did not rise about −10°. The resulting mixture was then stirred for 20 minutes at −12° to −15°. It was then cooled to −20° and the THF solution of silylated 7-amino-3-(1,2,3-triazol-5-ylthiomethyl)-3-cephem-4-carboxylic acid was added all at once. The temperature rose to about −12°. External cooling was discontinued until the temperature rose to 0°. At this point an ice-water bath was applied and the mixture stirred for 3 hours at 2°–3°. This was followed by a period of 1 hour without external cooling, the temperature rising to 20°. A total of 30 ml. methanol was added and the stirring continued for 15 minutes at room temperature. After evaporating the solvents under reduced pressure, the residue was suspended in 300 ml. ethyl acetate. The suspended solid was filtered off, (11.8 g.). The ethyl acetate solution was extracted three times with NaHCO$_3$ (5%) solution. The combined sodium bicarbonate extracts were cooled in an ice-bath, layered with ethyl acetate and acidified to a pH of 2.5 with 42.5% $H_3PO_4$. The phases were shaken and then separated. The ethyl acetate solution was then dried by passing it through sodium sulfate and then evaporated to about 15–20 ml. This solution was then added dropwise to stirred cyclohexane (~400 ml.) contained in an Erlenmeyer flask. After stirring for ½ hour the precipitated solid was collected by filtration. The collected, solid 7-[D-α-t-butoxycarbonylamino-α-(p-hydroxyphenyl)acetamido]-3-(1,2,3-triazol-5-ylthiomethyl)-3-cephem-4-carboxylic acid was air dried. It weighed 1.75 g.

7-[D-α-t-Butoxycarbonylamino-α-(p-hydroxyphenyl)-acetamido]-3-(1,2,3-triazol-5-ylthiomethyl)-3-cephem-4-carboxylic acid, 3.5 g., was dissolved in 80 ml. HCOOH, 98–100%, and stirred for 2 hours at room temperature. The HCOOH was evaporated under reduced pressure (aspirator bath temperature not above 40°) and finally azeotroped 3 times with 30 ml. of toluene. The solid was dried overnight under high vacuum over $P_2O_5$. A total of 3.5 g. of foam was obtained. The foam, 2 g., was stirred with 300 ml. of $H_2O$: $CH_3OH$ (8:2). The solvent was filtered from some solid (0.3 g.). charcoaled with 700 mg. of "Darko KB", filtered through diatomaceous earth ("Celite") and freeze-dried to yield 0.9 g. of crude 7-[D-α-amino-α-(p-hydroxyphenyl)acetamido]-3-(1,2,3-triazol-5-ylthiomethyl)-3-cephem-4-carboxylic acid. To crystallize the following procedure was used. A suspension of 0.2 g. of the crude material in 6 ml. of 99% methanol was heated in a test tube to boiling. Immediately the heating was discontinuted and the melt triturated with seeds. The melt solidified to a crystalline mass. In this manner a total of 0.211 g. of 7-[D-α-amino-α-(p-hydroxyphenyl)acetamido]-3-(1,2,3-triazol-5-ylthiomethyl)-3-cephem-4-carboxylic acid was obtained from 0.400 g. of crude material. The material was dried at 56°/0.1 mm over $P_2O_5$ for 20 hrs., m.p. >200° dec. IR and NMR are consistent with structure. The NMR indicates also the presence of ⅓ mole of $CH_3OH$.

Anal. Calcd. for $C_{18}H_{18}N_6O_5S_2.H_2O.1/3CH_3OH$: C, 44.83; H, 4.38; N, 17.10; S, 13.09.
Found: C, 43.97; H, 4.36; N, 15.84; S, 6.18.

A total 6.5 g. (11.55 mmole) of 7-[D-α-t-butoxycarbonylamino-α-(p-hydroxyphenyl)acetamido]-3-(1,2,3-triazol-5-ylthiomethyl)-3-cephem-4-carboxylic acid was dissolved in 175 ml. of 98–100% formic acid under anhydrous conditions. The mixture was stirred at room temperature for 2.5 hours. Part of the solution, 125 ml., was evaporated under reduced pressure to an amber oil. The oil was then azeotroped 3 times with 70 ml. of toluene under reduced pressure. The residue was suspended in an 80:20 $H_2O$-$CH_3OH$ solution (700 ml.) and stirred for 0.5 hour until most of the solid dissolved, then filtered. The filtration was treated with 1.5 g. of ("Darko") charcoal for about 20 minutes. The charcoal was filtered off through a "Celite" pad. The solution was then freeze-dried in 9 separate 100 ml. round bottom flasks. The freeze-dried material weighed 2.415 g. It was recrystallized in batches of 0.200 g. as described above to yield a total of 0.923 g. 7-[D-α-amino-α-(p-hydroxyphenyl)acetamido]-3-(1,2,3-triazol-5-ylthiomethyl)-3-cephem-4-carboxylic acid. NMR was consistent, indicating the presence of a ⅓ mole of $CH_3OH$.

Anal. Calcd. for $C_{18}H_{18}N_6O_5S_2.H_2O.⅓CH_3OH$: C, 44.83; H, 4.38; N, 17.10; S, 13.09.
Found: C, 45.77, 44.36; H, 4.44, 4.34; N, 16.61, 16.52; S, 13.01, 13.01.

The acylation of 7-amino-3-(1,2,3-triazol-5-yl-thiomethyl)-3-cephem-4-carboxylic acid (7-TACA) to BL-S640 has been carried out in methylene chloride with D-(-)-p-hydroxyphenylglycyl chloride hydrochloride. The yield to BL-S640 methanol solvate was about 45% on a biopotency basis. There was about 15% activity in the mother liquor and about 25% insoluble solids which is unreacted 7-TACA and 7-TACA decomposition product with degraded β-lactam.

The process essentially entails silylation with HMDS of 7-TACA in methylene chloride and then acylation with acid chloride.HCl at 0°–5°C. followed by methanol quench. The reaction is then stripped of methylene chloride and the methanol solution is "Darco KB" treated. The filtrate is vacuum concentrated and then adjusted to pH 4.8 – 5.0 with concentrated $NH_4OH$, seeded and crystallized.

EQUATIONS

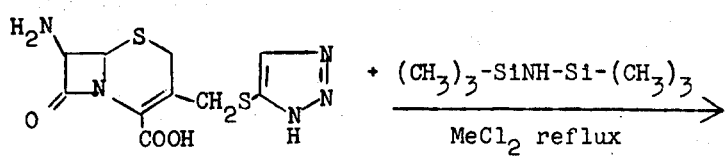

313.3
7-TACA (U.S. 3,759,904)

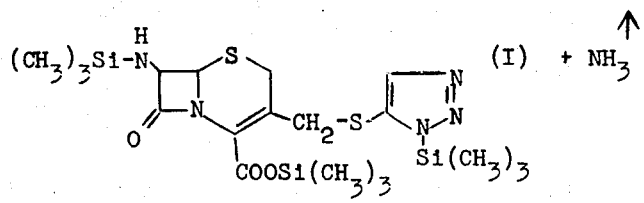

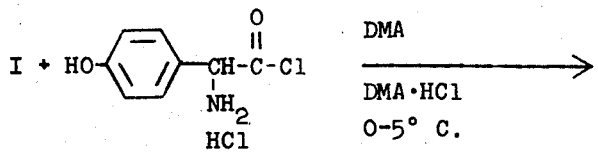

222

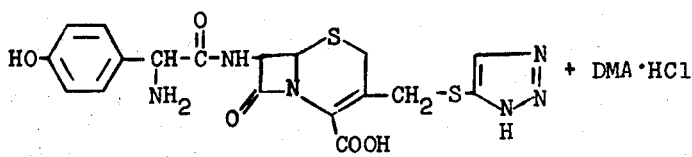

462.45
II

| MATERIALS: (Based on 1.0 kg. of 7-TACA) | | | |
|---|---|---|---|
| Reagent | g | ml. | Moles |
| 7-TACA | 1000.0 | | ~3.20 |
| D-(-)-p-hydroxyphenyl-glycylchloride.HCl | 797.0 | | ~3.60 |
| HMDS (Hexamethyldisilazane) | 965.0 | 1245.0 | ~5.95 |
| DMA.HCl (30% in MeCl₂) | | 320.0 | |
| DMA (Dimethylaniline) | | 480.0 | ~3.78 |
| Methylene chloride (Dry <0.01% KF) | As required | | |
| Methanol (Dry 0.01% KF) | " | | |
| Ammonium hydroxide | " | | |
| "Darco KB" (activated charcoal) | " | | |
| Imidazole | 21.8 | | 0.32 |

PROCEDURE 1. 1000 g. (3.20 moles) of 7-TACA is added to 25 liters of dry methylene chloride (K.F. H$_2$O <0.01%). The slurry is stirred and 1245 ml. (about 5.95 moles) of HMDS is added to the slurry.

2. The slurry is warmed to reflux and dry nitrogen gas is bubbled through the slurry. The refluxing is continued until complete solution and no settleable solids are noted. Batches of 7-TACA were refluxed for 12–22 hours to obtain a solution that was turbid.

3. After the silylation step is completed, the solution is cooled to about 15°–20° C. and 320 ml. of DMA.HCl (30% in MeCl₂) is added followed by 480 ml. of DMA (dimethylaniline) and 21.8 g. of imidazole. The reaction mix is chilled to 0°–5° C. and 797 g. (3.60 moles) of D-(−)-p-hydroxyphenylglycylchloride.HCl is added in 5 increments over a period of one hour. The slurry is stirred at 0°–5° C. for 10–12 hours or until all the acid chloride goes into solution.

4. The reaction mixture is warmed slowly over 3 hours to 20° C. and held for 2 hours at 20° C. Complete solution of the acid chloride should be noted.

5. 8.3 Liters of dry methanol (KF<0.01%) is added to the solution within one minute with good stirring. The mixture is stirred for 10–15 minutes and then immediately filtered very rapidly to remove insolubles. (In the laboratory, the filtration was carried out on a Buchner funnel and the cake was washed with a wash made up of two parts dry $MeCl_2$ and one part dry methanol.) This filtration must be done rapidly and the filtration setup prepared before hand so the filtration can be carried out as stated. The filtrate and wash had solids coming out after filtration. It is not known if these solids were product (possible .HCl salt). It may be that as the reaction with methanol takes place or due to take up of moisture in the laboratory hydrolysis of the silyl ester takes place and product starts to come out. The dark solids filtered out in this step contain some product, 7-TACA and degraded 7-TACA. The wash on the cake scales up to about 10 liters of $MeCl_2$-MeOH (2–1).

6. The filtrate and wash is vacuum concentrated to remove the $MeCl_2$ and dry methanol is added as necessary. The solution is concentrated to about 15–18 liters and 600 g. of "Darco KB" is added. The slurry is stirred for 20–25 minutes and then the slurry is filtered through a diatomaceous earth ("Dicalite") precoat and the cake is washed well with 8.0 liters of methanol. This treatment usually gives a yellow-orange filtrate.

7. The filtrate is vacuum concentrated to 12.0 – 13.0 liters and 480 ml. of deionized water is added to the solution. The pH will be in the 2.4 – 3.2 range. The solution is titrated slowly over 30 minutes to pH 4.8 – 5.0 with concentrated ammonium hydroxide. A scaleup of laboratory results would require 420 – 440 ml. of ammonium hydroxide. The solution is seeded when the pH has been adjusted to 4.0. The pH adjustment is carried out at 20° C. after which the slurry is stirred for 1 hour at 20° C. and then chilled to 0° C. for 16 hours. In the laboratory, after 3 hours stirring in an ice bath the beaker is packed in ice and held in the refrigerator overnight. Crystal growth on the sides of the beaker has always been noted after overnight holding. It is not known at this time if shorter hold time is adequate. However, 3 hours is not adequate from these visual observations. The precipitated product is collected by filtration, washed with MeOH (about filtrate volume) and dried at 45°. The usual yield is 750 – 770 g. of methanol solvate of 7-[D-α-amino-α-(p-hydroxyphenyl)acetamido]-3-(1,2,3-triazol-5-yl-thiomethyl)-3-cephem-4-carboxylic acid.

This procedure is an anhydrous one and all precautions are necessary to avoid water contamination or sweating that could cause hydrolysis of the silyl ester and subsequent poor acylation.

Preparation of Crystalline Methanol Solvate of 7-[D-α-amino-α-(p-hydroxyphenyl)acetamido]-3-(1,2,3-triazol-5-ylthiomethyl)-3-cephem-4-carboxylic acid 1. Fifty grams of 7-(D-α-amino-α-(p-hydroxyphenyl)-acetamido]-3-(1,2,3-triazol-5-ylthiomethyl)-3-cephem-4-carboxylic acid is slurried in 250 ml. of 95% V/V methanol/water (95% methanol) solution, at 22°–25° C.

2. Concentrated hydrochloric acid is added with rapid stirring to a pH of 1.3 – 1.5. A solution or near solution is obtained.

3. Adjust the pH to 1.7 with triethylamine.

4. Add 7.5 grams of activated charcoal ("Darco G-60") and slurry for 0.5 hours.

5. The carbon is removed by filtration and washed with 75 ml. of methanol which is added to the filtrate. Steps 2, 3 and 4 should be completed within 5 hours.

6. The combined wash and filtrate of Step 5 is rapidly stirred. Triethylamine is added over a 5 minute period to pH 4.5. Crystallization starts in about 1–3 minutes. The mixture is slurried for one hour.

7. The crystals are collected by filtration, washed with 100 ml. of methanol and vacuum dried at 56° C. — 24 hours. Bio yield 75–90%; bio-assay = 850–900 mcg./mg.; NMR-IR = Consistent for 1 mole of methanol; % $H_2O$, KF = 2–4.0.

Preparation of Crystalline BL-S640 1,2-Propylene Glycol Solvate

1. Twenty-five grams of the methanol solvate of 7-[D-α-amino-α-(p-hydroxyphenyl)acetamido]-3-(1,2,3-triazol-5-ylthiomethyl)-3-cephem-4-carboxylic acid prepared above is slurried in 150–200 ml. of 75% V/V propylene glycol-water solution at 20°–25° C.

2. Concentrated hydrochloric acid is added to a pH of 1–1.2 to obtain a solution or near solution.

3. Triethylamine (TEA) is slowly added with rapid stirring to obtain a pH of 1.7 – 1.8.

4. Five grams of "Darco G-60" is added and the mixture is slurried for 0.5 hour. The carbon is removed by filtration (filtration is slow, an 18.5 cm. SS No. 576 paper is suggested). The carbon filter cake is washed with 40 ml. of 75% V/V propylene glycol water solution. The wash is added to the filtrate. Steps 2, 3 and 4 above should be completed within 5 hours.

5. Triethylamine is added to pH 4.5 over a 10 minute period to the rapidly stirring filtrate - wash mixture of Step 4. Crystals form in about 1–3 minutes. The mixture is slurried for 1 hour.

6. The crystals of the propylene glycol solvate of 7-[D-α-amino-α-(p-hydroxyphenyl)acetamido]-3-(1,2,3-triazol-5-ylthiomethyl)-3-cephem-4-carboxylic acid are collected by filtration. Filtration is slow (a 12.5 – 15.0 cm. SS No. 576 paper is suggested). The crystals are washed consecutively with 50 ml. of 75% propylene glycol, 50 ml. of methanol, 50 ml. of acetone and vacuum dried at 56° C. for 24 hours. Biological yield: 80–95%.

Properties of
7-[D-α-amino-α-(p-hydroxyphenyl)acetamido]-3-(1,2,3-triazol-5-ylthiomethyl)-3-cephem-4-carboxylic acid propylene glycol solvate.

a. Bio-assay = 750–790 mcg./mg.

b. IR-NMR = Consistent for a structure containing 1.3 – 1.5 MOLES of propylene glycol (17–19% porpylene glycol). No loss of the 3-triazole side chain evident.

c. % Water, K.F. = 1–3.0.

d. Crystal morphology = 100% crystalline microcrystals, triangular shaped.

e. M.P. = 182°–184° C. (D, hot stage).

f. $[\alpha]_d^{25}$ (C = 1%; 1N-HCl) = +53°.

g. Water solubility = Approximately 10 mg./ml. in water at 23° C.

h. Loss of bioactivity on storage at elevated temperatures: 100° C., 24 hours = <6%; 48 hours = <12%; 56° C., 1 month = <10%.

Preparation of Crystalline Methanol Solvate from Crystalline Propylene Glycol Solvate The propylene glycol solvate of 7-[D-α-amino-α-(p-hydroxyphenyl)acetamido]-3-(1,2,3-triazol-5-ylthiomethyl)-3-cephem-4-carboxylic acid (50 g.) as prepared above is slurried in 250 ml. of 95% (volume/volume) methanol-water solution at 22°–25° C. Concentrated HCl is added with rapid stirring to a pH of 1.3–1.5 whereupon a solution or near solution is obtained. The pH is adjusted to 1.7 with triethylamine and 7.5 g. of activated charcoal is added with slurrying for 0.5 hours. The charcoal is removed by filtration and washed with 75 ml. of methanol. The wash solution is then added to the filtrate. (The steps from addition of the HCl to this point should be completed within 5 hours). The combined wash and filtrate is rapidly stirred and triethylamine added over a 5 minute period until a pH of 4.5 is reached. Crystallization starts in about 1–3 minutes. The mixture is slurried for 1 hour, and the crystals are removed by filtration, washed with 100 ml. methanol and vacuum dried at 56° C. for 24 hours. Bio Yield 75–90%; bio-assay = 850–900 mcg./mg.; NMR-IR = consistent for 1 mole of methanol; % $H_2O$, K.F. = 2–4.0.

The following examples are given in illustration of, but not in limitation of, the present invention.

DESCRIPTION OF THE PREFERRED EMBODIMENTS

EXAMPLE 1

Preparation of Crystalline
7-[D-α-amino-α-(p-hydroxyphenyl)acetamido]-3-(1,2,3-triazol-5-ylthiomethyl)-3-cephem-4-carboxylic acid sesquihydrate 7-[D-α-amino-α-(p-hydroxyphenyl)acetamido]-3-(1,2,3-triazol-5-ylthiomethyl)-3-cephem-4-carboxylic acid methanol solvate (3.0 g.) was slurried in 20 ml. water for 18 hours at room temperature to give a pH 3.9 suspension. The crystals were removed by filtration and washed with 5 ml. of water. An aliquot was air dried at 45° C. for 24 hours to give the title crystalline product. % $H_2O$, K.F. = 5.54 (theoretical for sesquihydrate = 5.51). Melting point = 188°–194° C. (decomposition). IR and NMR analyses were consistent for the proposed structure and indicated that the product contained no methanol.

EXAMPLE 2

7-[D-α-amino-α-(p-hydroxyphenyl)acetamido]-3-(1,2,3-triazol-5-ylthiomethyl)-3-cephem-4-carboxylic acid sesquihydrate 7-[D-α-amino-α-(p-hydroxyphenyl)acetamido]-3-(1,2,3-triazol-5-ylthiomethyl)-3-cephem-4-carboxylic acid methanol solvate (15 g.) was slurried in 60 ml. of water. The pH was raised to 6.5 by addition of 4N NaOH and the mixture was passed through a 200 mesh screen. The reaction mixture was slurried at room temperature for 2 hours, the pH being maintained at 6.5 during this period. The crystals were removed by filtration, washed with 20 ml. of water and air dried at 37° C. for 24 hours to give 11.5 g. of title crystalline product. Bio assay = 924 mcg./mg. (average). % $H_2O$, K.F. = 5.26. NMR and IR were consistent for the proposed structure and indicated that the product contained no methanol but did have a trace of propylene glycol.

EXAMPLE 3

Preparation of Crystalline
7-[D-α-amino-α-(p-hydroxyphenyl)acetamido]-3-(1,2,3-triazol-5-ylthiomethyl)-3-cephem-4-carboxylic acid sesquihydrate and formation of other crystalline hydrates 7-[D-α-Amino-α-(p-hydroxyphenyl)acetamido]-3-(1,2,3-trizol-5-ylthiomethyl)-3-cephem-4-carboxylic acid methanol solvate (200 mesh; 10.0 g.) substantially free of propylene glycol is slurried in 30–40 ml. of deionized water at ambient room temperature (20°–25° C.) to give a pH 3–4 aqueous suspension. NaOH (40%) is slowly added with rapid stirring to bring the pH to 6.3 – 6.7. The mixture is slurried at pH 6.3–6.7 for 2 hours. The crystals are removed by filtration, washed with water and air dried at room temperature for 24 hours to give a 75–80% weight yield of 950–1000 mcg./mg. crystals of 7-[D-α-Amino-α-(p-hydroxyphenyl)-acetamido]-3-(1,2,3-triazol-5-ylthiomethyl)-3-cephem-4-carboxylic acid dihydrate. IR and MNR analyses were consistent for the proposed structure and indicated that the product contained no methanol but did have a trace of propylene glycol. $H_2O$, K.F. = 6.56.

A sample of the crystalline dihydrate was air dried at 37° C. for 24 hours giving the crystalline sesquihydrate of 7-[D-α-Amino-α-(p-hydroxyphenyl)acetamido]-3-(1,2,3-triazol-5-ylthiomethyl)-3-cephem-4-carboxylic acid. $H_2O$, K.F. = 5.26.

A second sample of the dihydrate was air dried at 45° C. for 24 hours to give the crystalline sesquihydrate. $H_2O$, K.F. = 5.5.

A sample of the dihydrate was air dried at 56° C. for 24 hours to give the crystalline monohydrate of 7-[D-α-Amino-α-(p-hydroxyphenyl)acetamido]-3-(1,2,3-triazol-5-ylthiomethyl)-3-cephem-4-carboxylic acid. $H_2O$, K.F. = 4.38 (theoretical % $H_2O$ for monohydrate = 3.75).

A sample of the dihydrate was vacuum dried over $P_2O_5$ at room temperature for 24 hours giving the crystalline hemihydrate of 7-[D-α-Amino-α-(p-hydroxyphenyl)acetamido]-3-(1,2,3-triazol-5-ylthiomethyl)-3-cephem-4-carboxylic acid. $H_2O$, K.F. = 2.63 (theoretical % $H_2O$ for hemihydrate — 1.91).

A sample of the dihydrate was vacuum dried at 56° C. for 24 hours giving the crystalline hemihydrate. $H_2O$, K.F. = 1.6 – 2.0.

EXAMPLE 4

7-[D-α-amino-α-(p-hydroxyphenyl)acetamido]-3-(1,2,3-triazol-5-ylthiomethyl)-3-cephem-4-carboxylic acid sesquihydrate (micronized) for Intramuscular Suspension Formula

| | Per 1 Dose | Per 15 Doses |
|---|---|---|
| Sterile, micronized 7-[D-α-amino-α-(p-hydroxyphenyl)-acetamido]-3-(1,2,3-triazol-5-ylthiomethyl)-3-cephem-4-carboxylic acid sesquihydrate | 0.275 g. (equiv. to 250 mg. of BL-S640 activity) | 4.125 g. |
| Lecithin | 0.002 | 0.030 |
| Methylparaben | 0.0009 | 0.0135 |

Formula-continued

|  | Per 1 Dose | Per 15 Doses |
|---|---|---|
| Propylparaben | 0.0001 | 0.0015 |
| Polyvinylpyrrolidone (Povidone) | 0.005 | 0.075 |
| Sodium chloride | 0.002 | 0.030 |
| Tween 80 | 0.001 | 0.015 |

The BL-S640 sesquihydrate to be used must be sterile, pyrogen free and handled aseptically throughout the processing.

Intramuscular BL-S640 Sesquihydrate (Micronized)
(Label claim is 250 mg./ml. BL-S640 activity as BL-S640 Sesquihydrate 1. The BL-S640 sesquihydrate to be used must be sterile, pyrogen free and handled aseptically throughout the processing.
2. The BL-S640 sesquihydrate is sterilely micronized in a sterile micronizer.
3. The sterile micronized BL-S640 sesquihydrate plus the sterile sodium chloride is then loaded into a sterile Patterson Kelly V Blender equipped with an intensification bar adapted for liquid addition. The blender has been rendered sterile by spraying with peracetic acid and exposure to ethylene oxide gas for 16 hours prior to use. Care must be taken, before blender is loaded, so that no condensation of the gases has occurred inside the blender. The condensation may be prevented by obtaining proper atmospheric room temperature. The blender is run for 30 minutes with intensification action to assure initial blending of the material.
4. The lecithin, methyl and propyl parabens, Tween-80 and Povidone are dissolved in a volume of methylene chloride equal to approximately one-fifth (1/5) the weight of BL-S640 sesquihydrate required.
5. Using aseptic conditions, the solution of Step 4 is passed, under positive pressure through a sterile 0.22 micron Millipore filter into an appropriate sterile container located in a sterile area.
6. Using the "liquid addition apparatus" of the blender, add the required volume of sterile, pyrogen-free methylene chloride solution of Step 5 in five equal portions. After each addition of solution the intensification bar is utilized for a maximum of 2 minutes using 4 "agitation" periods during the 15 minutes blending period required for each addition of solution. At the termination of each blending period the pressure developed during the blending process must be released (noted on gauge on shell of blender) and vacuum applied to remove the methylene chloride vapors. This must be repeated to assure complete removal of vapors. To aid in the evaporation and removal of vapors heat at 115°F may be applied to the shell by circulating hot water through the walls.
7. When all the solution has been added and blend properly vacated of vapors the material is dropped from the blender and trayed for drying. The material is placed in covered trays and placed in a hot air atmospheric oven and dried for 6 hours. The temperature of heated air should not exceed 130°F. After 6 hours of heating, the heat is turned off and air circulated over the trays for 10 hours to assure complete drying.
8. Repulverize the coated material utilizing the procedure of Step 2 so that the following requirement is met:

Retained on a 200 Mesh Screen 0.1% Maximum

9. Collect into sterile containers as a finished bulk product for final disposition.
10. The proper amount of coated BL-S640 sesquihydrate is filled, using aseptic technique, into officially designated size silicone coated vials.

EXAMPLE 5

Preparation of Solution of
7-[D-α-amino-α-(p-hydroxyphenyl)acetamido]-3-
(1,2,3-triazol-5-ylthiomethyl)-3-cephem-4-carboxylic
acid sesquihydrate for use in intramuscular or
intravenous dosage form.

Formula

|  | Per 4 ml. |  |
|---|---|---|
| BL-S640 sesquihydrate | 1.08 g. | (equivalent to 250 mg./ml. BL-S640 activity) |
| Sodium bicarbonate | 0.27 g. |  |
| Deionized water | 3.0 g. |  |

The above components are shaken to form an amber solution having a pH = 7.1. The solution was allowed to stand at room temperature and periodically assayed to determine stability. The assay results are as follows:

| Time | Bioassay | % Loss |
|---|---|---|
| 0 | 240 mg./ml. | — |
| 15 minutes | 238 | − 0.8 |
| 30 minutes | 238 | − 0.8 |
| 60 minutes | 226 | − 5.8 |
| 90 minutes | 220 | − 8.3 |
| 2 hours | 202 | −15.9 |

The above 250 mg./ml. solution is stable for at least 90 minutes at room temperature and is an acceptable IM or IV dosage form.

Biological Data

A sample of BL-S640 sesquihydrate after solution in water and dilution with Nutrient Broth was found to exhibit the following Minimum Inhibitory Concentrations (M.I.C.'s) in mcg./ml. versus the indicated microorganisms as determined by overnight incubation at 37° C. by Tube Dilution. Table I below also includes M.I.C. values for cephalexin, a commercial orally absorbed cephalosporin.

Table II below compares BL-S640 sesquihydrate and cephalexin with respect to blood levels in mice after oral administration. Table III below compares BL-S640 sesquihydrate and sodium cefazolin with respect to blood levels in mice after intramuscular administration.

Table I

| Organism | M.I.C. (µg./ml.) | BL-S640 Sesquihydrate | Cephalexin |
|---|---|---|---|
| D. pneumoniae at 10⁻³ + 5% serum[1] dil'n | A9585 | 0.02 | 0.08 |
| Str. Pyogenes at 10⁻³ + 5% serum[1] dil'n | A9604 | 0.02 | 0.08 |
| S. aureus Smith[2] | A9537 | 0.3 | 0.6 |
| S. aureus Smith[2] + 50% serum | A9537 | 1 | 2.5 |
| S. aureus BX1633-2 at 10⁻³ dil'n | A9606 | 0.6 | 1 |
| S. aureus BX1633-2 | A9606 | 2 | 2 |

Table I-continued

| Organism | | M.I.C. (μg./ml.) BL-S640 Sesquihydrate | Cephalexin |
|---|---|---|---|
| at 10$^{-2}$ dil'n | | | |
| S. aureus(methicillin resist) at 10$^{-3}$ dil'n | A15097 | 8 | 32 |
| Sal.enteritidis[2] | A9531 | 0.6 | 2 |
| E. coli Juhl[2] | A15119 | 2 | 4 |
| E. coli[2] | A9675 | 4 | 16 |
| K. pneumoniae[2] | A9977 | 1 | 2 |
| K. pneumoniae[2] | A15130 | 2 | 8 |
| Pr. mirabilis[2] | A9900 | 0.5 | 2 |
| Pr. morganii[2] | A15153 | 16 | >125 |
| Ps. aeruginosa[2] | A9843A | >125 | >125 |
| Ser. marcescens[2] | A20019 | 125 | >125 |
| Ent. cloacae[2] | A9656 | >125 | >125 |
| Ent. cloacae[2] | A9657 | 1 | 2 |
| Ent. cloacae[2] | A9659 | 32 | >125 |

[1] 50% Nutrient Broth - 45% Antibiotic Assay Broth
[2] at 10$^{-4}$ dilution

Table II

Mouse Blood Levels after Oral Administration of 100 mg./kg. Body Weight BL-S640 Sesquihydrate

| Compound | No. of mice | Blood Levels (μg./ml.) | | | |
|---|---|---|---|---|---|
| | | 0.5 | 1 | 2 | 3.5 |
| | | Hr. after Administration | | | |
| BL-S640 Sesquihydrate | 8 | 46.0 | 42.5 | 22.5 | 11.9 |
| Cephalexin Monohydrate | 32 | 42.4 | 26.9 | 8.5 | <4.6 |

Table III

Mouse Blood Levels after IM Administration of 10 mg./kg. Dose of BL-S640 Sesquihydrate

| Compound | Blood Levels (μg./ml.) | | | |
|---|---|---|---|---|
| | 5 | 30 | 60 | 90 |
| | Min. after Administration | | | |
| BL-S640 Sesquihydrate | 15.0 | 13.5 | 9.4 | 6.8 |
| Cefazolin, Na salt | 16.1 | 11.1 | 5.7 | 2.9 |

We claim:
1. Crystalline 7-[D-α-amino-α-(p-hydroxyphenyl)-acetamido]-3-(1,2,3-triazol-5-ylthiomethyl)-3-cephem-4-carboxylic acid sesquihydrate exhibiting essentially the following X-ray powder diffraction properties:

| Line | Spacing d(A) | Relative Intensity |
|---|---|---|
| 1 | 9.31 | 45 |
| 2 | 6.77 | 93 |
| 3 | 6.17 | 32 |
| 4 | 5.56 | 14 |
| 5 | 4.42 | 100 |
| 6 | 3.97 | 76 |
| 7 | 3.78 | 95 |
| 8 | 3.55 | 55 |
| 9 | 3.41 | 53 |
| 10 | 3.10 | 26 |
| 11 | 3.01 | 19 |
| 12 | 2.94 | 9 |
| 13 | 2.83 | 17 |
| 14 | 2.77 | 23 |
| 15 | 2.55 | 19 |
| 16 | 2.32 | 10 |
| 17 | 2.23 | 12 |
| 18 | 2.05 | 10 |
| 19 | 1.97 | 6 |
| 20 | 1.88 | 7. |

* * * * *